United States Patent
Lerner

[11] Patent Number: 5,956,963
[45] Date of Patent: Sep. 28, 1999

[54] WRIST COOLER FOR RELIEF OF HOT FLASHES AND SIMILAR SYMPTOMS

[76] Inventor: Irene K. Lerner, 3533 R.F.D., Long Grove, Ill. 60047

[21] Appl. No.: 08/784,763

[22] Filed: Jan. 16, 1997

Related U.S. Application Data

[60] Provisional application No. 06/010,199, Jan. 18, 1996.

[51] Int. Cl.[6] ............... F25D 23/12; F25D 3/08; A61F 7/00
[52] U.S. Cl. .................. 62/259.3; 62/4; 62/530; 607/96; 607/114
[58] Field of Search .............. 62/4, 259.3, 530; 607/96, 108, 114

[56] References Cited

U.S. PATENT DOCUMENTS

| | | | |
|---|---|---|---|
| 1,941,173 | 12/1933 | Lark-Horovitz | 62/331 |
| 2,288,745 | 7/1942 | Sammis | 62/331 |
| 2,715,315 | 8/1955 | Giardini | 62/331 |
| 3,149,943 | 9/1964 | Amador | 62/4 |
| 3,865,117 | 2/1975 | Perry | 62/4 |
| 3,950,158 | 4/1976 | Gossett | 62/4 |
| 4,625,729 | 12/1986 | Roney . | |
| 4,972,832 | 11/1990 | Trapini et al. . | |
| 5,005,374 | 4/1991 | Spitler . | |
| 5,123,411 | 6/1992 | Noziri | 62/4 |
| 5,163,504 | 11/1992 | Resnick | 62/4 |
| 5,165,402 | 11/1992 | McCoy . | |
| 5,305,470 | 4/1994 | McKay . | |
| 5,415,624 | 5/1995 | Williams . | |

*Primary Examiner*—William Doerrler
*Attorney, Agent, or Firm*—James Creighton Wray; Meera P. Narasimhan

[57] ABSTRACT

The invention offers relief for hot flash symptoms of menopause and body overheating by providing a wrist cooler. The cooler preferably includes chemical cooling pellets that remain in a solid state until broken. A woman experiencing symptoms such as menopausal hot flashes carries the cooler in her purse. When hot flashes occur, the cooler is removed from her purse, the pellets are broken and the cooler is slid onto her wrist. Once the flashes have subsided, the cooler is discarded. The invention is easily transportable and provides for immediate relief, as there are no reusable cooling elements to be frozen or chilled.

20 Claims, 1 Drawing Sheet

WRIST COOLER FOR RELIEF OF HOT FLASHES AND SIMILAR SYMPTOMS

This application claims the benefit of U.S. Provisional Application No. 60/010,199, filed Jan. 18, 1996.

SUMMARY OF THE INVENTION

The invention offers relief for hot flash symptoms of menopause and body overheating by providing a wrist cooler. The cooler preferably includes chemical cooling pellets that remain in a solid state until broken. A woman experiencing symptoms such as menopausal hot flashes carries the cooler in her purse. When hot flashes occur, the cooler is removed from her purse, the pellets are broken and the cooler is slid onto her wrist. Once the flashes have subsided, the cooler is discarded. The invention is easily transportable and provides for immediate relief, as there are no reusable cooling elements to be frozen or chilled.

Hot flashes and similar symptoms can be experienced by women of all ages. Since women are living longer lives, symptoms such as hot flashes not only are more commonly encountered but also are being openly discussed and relief more actively pursued.

The invention provides a non-pharmaceutical, quick and efficient way to relieve symptoms that women of all ages might experience.

The invention is a new system for relieving discomfort associated with menopause in a non-pharmaceutical manner. Cold is applied to the wrist with wrist wraps. When hot flashes occur unexpectedly, a wrist band carried in a purse has a cold pouch which is ready to operate at any time to relieve the discomfort of hot flashes. Alternatively, a decorative wrist band may be worn at other times, and when hot flashes occur the cooling qualities may be activated. Preferably the wrist band is a narrow and thin decorative band. The wrist band may be filled, partially filled or have a pouch containing frangible containers or mixable chemicals, or solids or fluids to cause quick chilling of wrists when desired.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
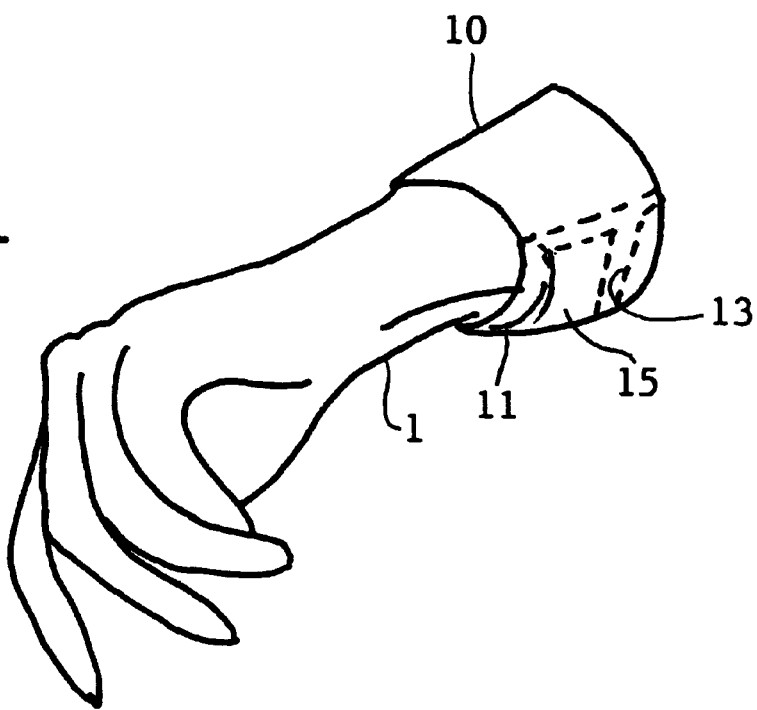
FIG. 1 shows a decorative wrist band with a pocket for cooling material on the underside of the wrist.

FIG. 1 shows a fabric wrist band 10 having a holder 11 positioned for lying against the underside of a wrist 1. Before use or before placing the wrist band 10 in a pocketbook, a pouch of cold-producing crystalline material is placed in the holder 11, and the flap 13 is closed inwardly to hold the pouch 15 within the holder.

The wrist band 10 with the pouch 15 inserted in the holder 11 is kneaded, fracturing and mixing crystalline material, causing transformation of the material and taking up localized body heat that flows through arteries and veins near the surface of the underside of the wrist. Pushing the wrist band into place helps to maintain the flap 13 closed so that a simple lightweight elastic wrist band may be used.

Figure 2:
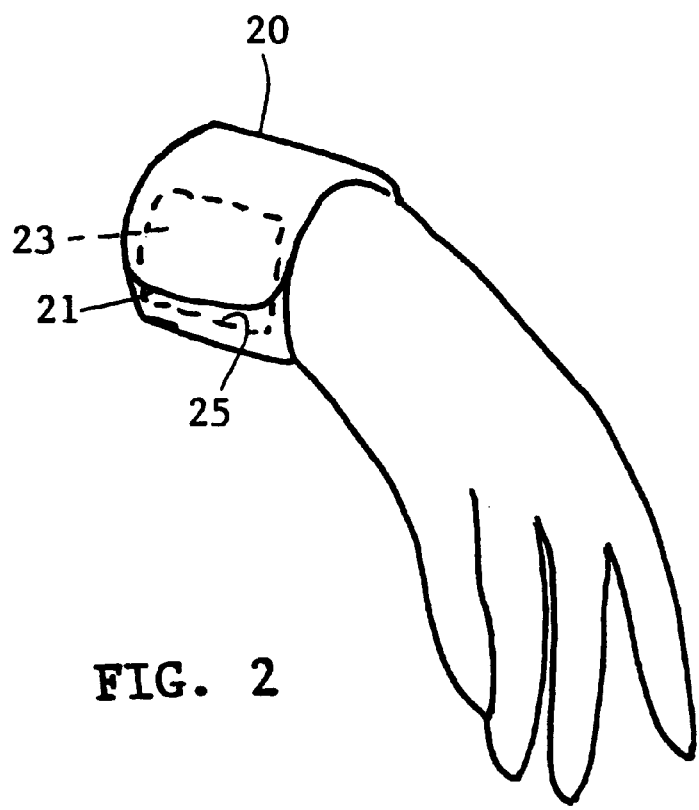
FIG. 2 shows a wrap-around wrist band that has a similar pocket for cooling material on the underside of the wrist.

An alternate form 20 of the wrist band is shown in FIG. 2. There the wrist band is a wrap, with one end 21 having micro hook fasteners 23 on its inner surface. The remainder of the band or a strip portion 25 has small loops which engage the miniature hooks 23 to wrap and secure the band 20 around the wrist.

The pouch with the crystalline heat absorbing material is held under the wrist. When the symptoms of discomfiture pass, the wrist band is removed and placed in a purse. If the symptoms reoccur, a new pouch is placed in the holder 11, and the pouch or the wrist band is kneaded to fracture the crystals or intermix the materials for heat absorbing, before the wrist band is slid over the wrist in the case of FIG. 1 or wrapped around the wrist in the case of FIG. 2.

The wrist band shown in FIGS. 1 and 2 may be thin and narrow and may be made of a decorative material. The wrist band may be made of metal or plastic and may have a decorative design similar to designs found in jewelry. The cross-section of the wrist band may be flat, rectangular, oval or circular, for example.

The invention is intended primarily for the non-pharmaceutical relief of hot flash symptoms due to menopause, and may be easily and conveniently carried and used and replaced or discarded after use. The preferred material of the wrist band 10 or 20 is a fabric material which is slightly stretchable to conform to the wrist. Alternatively, the material may be a flannel material, in which case the strips 23 and 25 are adhesive. Alternatively, the wrist band 10 may be a metallic wrist band with elastic inserts for giving the appearance of a decorative wide bracelet while aiding the conduction of heat away from the body for temporary relief of symptoms without pharmaceuticals.

Any suitable endothermic materials may be inserted in the pocket. For example, the materials may be in the form of frangible particles which, when crushed, sublimate or melt. The materials may be particles which, when crushed, react in an endothermic reaction. The particles may be encapsulated in frangible coatings or in breakable vials. Alternatively, evaporative crystals or liquids in breakable vials give the immediacy of response.

While the invention has been described with reference to specific embodiments, modifications and variations of the invention may be constructed without departing from the scope of the invention, which is defined in the following claims.

I claim:

1. A wrist band for wearing on a wrist and counteracting hot flashes without pharmaceuticals, comprising a wrist band, a pocket in one part of the wrist band located in contact with an underside of the wrist, and fracturable chemicals removably disposed in the pocket, wherein fracturing the chemicals allows cooling of the underside of the wrist on demand, for relief of hot flashes.

2. The apparatus of claim 1, wherein the band is elastic.

3. The apparatus of claim 1, wherein the band is made of fabric.

4. The apparatus of claim 1, wherein the band is made of plastic.

5. The apparatus of claim 1, wherein the band is made of metal.

6. The apparatus of claim 1, wherein the pocket has an inward tuckable flange for holding the chemical.

7. The apparatus of claim 1, wherein the chemicals are crystals which evaporate when crushed.

8. The apparatus of claim 1, wherein the chemicals are crystals which sublimate when crushed.

9. The apparatus of claim 1, wherein the chemicals are crystals which when fractured react in an endothermic reaction.

10. The apparatus of claim 1, wherein the chemicals are crystals which are contained in frangible vials.

11. The apparatus of claim 1, wherein the chemicals are fluids which are contained in frangible vials.

12. The method of combating hot flashes without pharmaceuticals, comprising removably inserting chemicals which produce cooling when fractured in a pouch of a wrist band, placing the wrist band on a wrist, positioning the pouch below the wrist, activating chemicals in the pouch upon onset of hot flashes, and producing endothermic cooling of the underside of the wrist on demand.

13. The method of claim 12, wherein the activating step comprises crushing frangible materials.

14. The method of claim 13, wherein the crushing precedes placing the band on the wrist.

15. The method of claim 13, wherein the crushing precedes inserting chemicals in the pouch.

16. The method of claim 13, wherein the crushing follows positioning the pouch below the wrist.

17. The apparatus of claim 1, wherein the wrist band is of one-piece.

18. The apparatus of claim 1, wherein the wrist band is flexible and is positionable by slipping on the wrist.

19. The apparatus of claim 1, wherein the wrist band is of one-piece and is attachable to the wrist by fasteners.

20. The apparatus of claim 1, wherein the pocket is invisible.

* * * * *